United States Patent [19]

Miller et al.

[11] Patent Number: 5,707,986

[45] Date of Patent: Jan. 13, 1998

[54] ANGIOGRAPHIC METHOD USING GREEN PORPHYRINS IN PRIMATE EYES

[76] Inventors: Joan W. Miller; Lucy H.Y. Young; Evangelos S. Gragoudas, all of c/o Retina Service, Massachusetts Eye & Ear Infirmary, 243 Charles St., Boston, Mass. 02114

[21] Appl. No.: 209,473

[22] Filed: Mar. 14, 1994

[51] Int. Cl.$^6$ .......................... A61K 31/40; A61K 47/42
[52] U.S. Cl. .......................... 514/185; 514/410; 514/912
[58] Field of Search .......................... 514/185, 410, 514/912

[56] References Cited

U.S. PATENT DOCUMENTS 5,171,749  12/1992  Levy et al. .
5,214,036  5/1993  Allison et al. .

OTHER PUBLICATIONS

Schmidt et al., "Photosensitizing Potency of Benzoporphyrin Derivative (BPD) Associated with Human Low Density Lipoprotein (LDL)", *IOVS*(1992) 33:1253 Abstract 2802.

Lin et al., "Measurement of BPD Photosensitizer Kinetics in Retinal and Choroidal Vessels by Fluorescence Imaging", *IOVS* (1933) 34:1168 Abstract 2293.

Lin et al., "Photodynamic Closure of Choroidal Vessels Using Benzoporphyrin Derivative", *IOVS* (1993) 34:1303 Abstract 2953.

Schmidt–Erfurth et al., "Photothrombosis of Ocular Neovascularization Using Benzoporphyrin (BPD)", *IOVS* (1993) 34:1303 Abstracts 2956.

Haimovici et al., "Localization of Benzoporphyrin Derivative Monoacid in the Rabbit Eye", *IOVS* (1993) 34:1303 Abstracts 2955.

Walsh et al., "Photodynamic Therapy of Experimental Choroidal Neovascularization Using Benzoporphyrin Derivative Monoacid", *IOVS* (1993) 34:1303 Abstracts 2954.

Moulton et al., "Response of Retinal and Choroidal Vessels to Photodynamic Therapy Using Benzoporphyrin Derivative Monoacid", *IOVS* (1993) 34:1169 Abstract 58.

Gonzales et al., "Photodynamic Therapy of Pigmented Choroidal Melanomas", *IOVS* (1993) 34:891 Abstract 949.

Schmidt–Erfurth et al., "Photodynamic Therapy of Experimental Choroidal Melanoma Using Lipoprotein–delivered Benzoporphyrin", *Ophthalmology* (1994) 101:89–99.

Pandey et al., "Efficient Synthesis of New Classes of Regiochemically Pure Benzoporphyrin Derivatives", *Bioorganic & Medicinal Chemistry Letters* (3)12:2615–2618 (1993).

*Primary Examiner*—Zohreh Fay
*Attorney, Agent, or Firm*—Morrison & Foerster LLP

[57] ABSTRACT

An angiographic method to observe the condition of blood vessels, including neovasculature in the eyes of living primates using green porphyrins and light at a wavelength of 550–700 nm to effect fluorescence is disclosed.

6 Claims, 1 Drawing Sheet

ANGIOGRAPHIC METHOD USING GREEN PORPHYRINS IN PRIMATE EYES

TECHNICAL FIELD

The invention is in the field of photodynamic therapy, specifically related to ocular conditions. More particularly, the invention concerns the use of green porphyrins in photodynamic therapeutic treatment of pigmented tumors and conditions characterized by unwanted neovasculature in the eye. Green porphyrins are also useful as dyes in ocular angiography.

BACKGROUND ART

Choroidal neovascularization leads to hemorrhage and fibrosis, with resultant visual loss in a number of eye diseases, including macular degeneration, ocular histoplasmosis syndrome, myopia, and inflammatory diseases. Age-related macular degeneration is the leading cause of new blindness in the elderly, and choroidal neovascularization is responsible for 80% of the severe visual loss in patients with this diseases. Although the natural history of the disease is eventual quiescence and regression of the neovascularization process, this usually occurs at the cost of sub-retinal fibrosis and vision loss.

Current treatment relies on occlusion of the blood vessels using laser photocoagulation. However, such treatment requires thermal destruction of the neovascular tissue, and is accompanied by full-thickness retinal damage, as well as damage to medium and large choroidal vessels. Further, the subject is left with an atrophic scar and visual scotoma. Moreover, recurrences are common, and visual prognosis is poor.

Developing strategies have sought more selective closure of the blood vessels to preserve the overlying neurosensory retina. One such strategy is photodynamic therapy, which relies on low intensity light exposure of photosensitized tissues to produce photochemical effects. Photosensitizing dyes are preferentially retained in tumors and neovascular tissue, which allows for selective treatment of the pathologic tissue. As a result of the invention, PDT may be used to cause vascular occlusion in tumors by damaging endothelial cells, as well as a direct cytotoxic effect on tumor cells.

Photodynamic therapy of conditions in the eye characterized by neovascularization has been attempted over the past several decades using the conventional porphyrin derivatives such as hematoporphyrin derivative and Photofrin porfimer sodium. Problems have been encountered in this context due to interference from eye pigments. In addition, phthalocyanine has been used in photodynamic treatment.

A newer photosensitizer, a member of the group designated "green porphyrins", is in the class of compounds called benzoporphyrin derivatives (BPD). This photosensitizer has also been tested to some extent in connection with ocular conditions. For example, Schmidt, U. et al. described experiments using BPD for the treatment of Greene melanoma (a nonpigmented tumor) implanted into rabbit eyes and achieved necrosis in this context (*IOVS* (1992) 33:1253 Abstract 2802). Lin, C. P. et al. describe the measurement of kinetics and distribution in retinal and choroidal vessels by fluorescence imaging using a 458 nm line from an argon-ion laser to excite BPD (*IOVS* (1993) 34:1168 Abstract 2293). In addition, Lin, S. C. et al. described photodynamic closure of choroidal vessels using BPD in *IOVS* (1993) 34:1303 Abstract 2953.

The present applicants have described treating choroidal neovascularization using BPD in several abstracts published 15 Mar. 1993 and incorporated herein by reference. These abstracts include Schmidt-Erfurth, U. et al. "Photothrombosis of Ocular Neovascularization Using BPD"; Haimovici, R. et al. "Localization of Benzoporphyrin Derivative Monoacid in the Rabbit Eye"; and Walsh, A. W. et al. "Photodynamic Therapy of Experimental Choroidal Neovascularization Using BPD-MA." All of the foregoing are published in *IOVS* (1993) 34:1303 as abstracts 2956, 2955 and 2954, and Moulton, R. S. et al. "Response of Retinal and Choroidal Vessels to Photodynamic Therapy Using Benzoporphyrin Derivative Monoacid", *IOVS* (1993) 34:1169 Abstract 58.

The green porphyrins offer advantages in their selectivity for neovasculature and in their ability to effect photodynamically mediated destruction of nonpigmented tumors of the eye. Gonzales et al. reported photodynamic therapy of pigmented melanomas in the eye using phthalocyanine as a photoactive compound (Gonzales, Y. H. et al. (*IOVS* (1993) 34:891 Abstract 949). The use of BPD-MA in photodynamic treatment of the nonpigmented Greene hamster melanoma in rabbit eyes was also described by Schmidt-Erfurth, U. et al. in *Ophthalmology* (1994) 101:89–99. This report was presented in part at the ARVO annual meeting in Sarasota, Fla., May 1992.

DISCLOSURE OF THE INVENTION

The invention is directed to diagnosis and treatment of certain conditions of the eye using photodynamic methods and employing green porphyrins as the photoactive compounds. The green porphyrins of the invention are described in U.S. Pat. Nos. 4,883,790; 4,920,143; 5,095,030; and 5,171,749, the entire contents of which are incorporated herein by reference. These materials offer advantages of selectivity and effectiveness when employed in protocols directed to the destruction of unwanted neovasculature and pigmented tumors. They are also particularly effective as visualizing agents in angiography of ocular blood vessels. The visualization of the compounds is enhanced by their ability to fluoresce.

Accordingly, in one aspect, the invention is directed to a method to treat conditions of the eye characterized by unwanted neovasculature, which method comprises administering to a subject in need of such treatment an amount of a green porphyrin that will localize in said neovasculature; and irradiating the neovasculature with light absorbed by the green porphyrin.

In another aspect, the invention is directed to a method to treat pigmented tumors in the eye, which method comprises administering to a subject in need of such treatment an amount of a green porphyrin that will localize in said tumor; and irradiating the tumor with light absorbed by the green porphyrin.

In still another aspect, the invention is directed to a method to observe the condition of blood vessels in the eye, which method comprises administering to a subject comprising at least one eye for which said observation is desired an amount of green porphyrin which will provide an observable amount of green porphyrin in the blood vessels of said eye, permitting sufficient time to elapse so that an observable amount of said green porphyrin resides in the eyes; and observing the blood vessels in which the green porphyrin resides.

MODES OF CARRYING OUT THE INVENTION

Figure 1A:
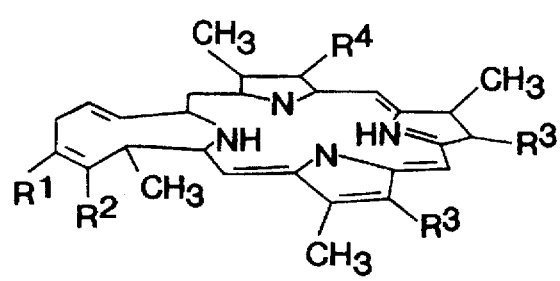
FIG. 1 shows preferred forms of the green porphyrins useful in the methods of the invention.
Figure 1B:
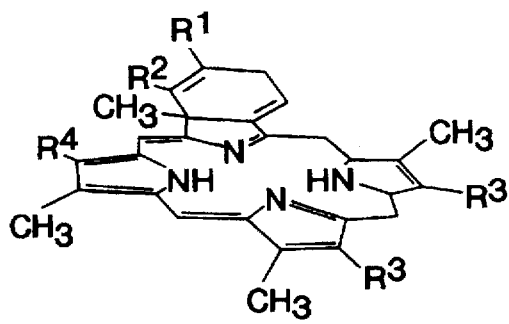
Figure 1C:
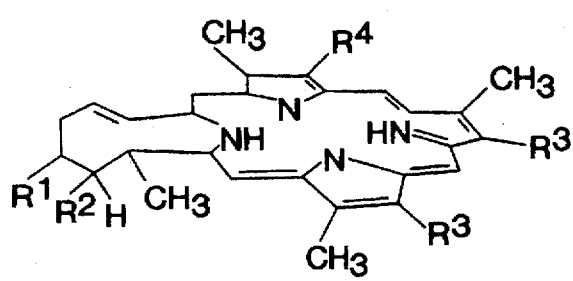
Figure 1D:
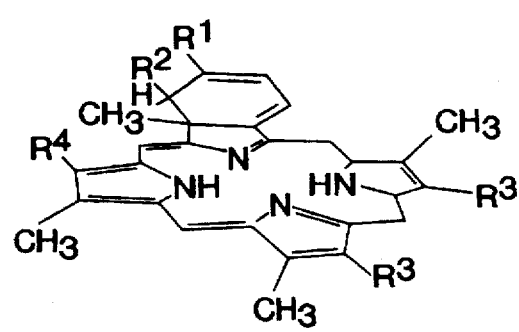
Figure 1E:
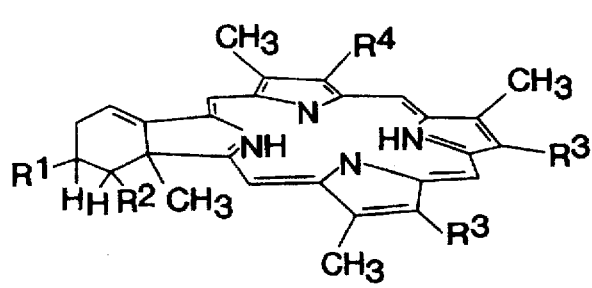
Figure 1F:
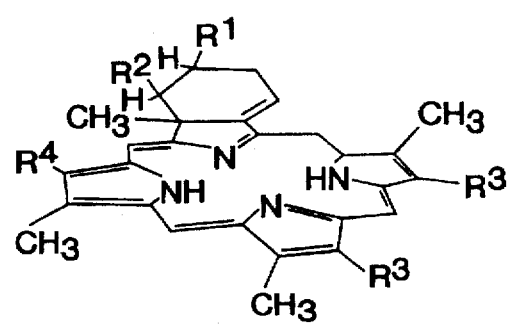

The methods of the claimed invention administering to a subject a green porphyrin, which is in the class of compounds called benzoporphyrin derivatives (BPD). A BPD is a synthetic chlorin-like porphyrin with a number of structural analogues, as shown in FIG. 1.

Preferably, the green porphyrin is benzoporphyrin derivative mono-acid ring A (BPD-MA), which absorbs light at about 692 nm wavelength with improved tissue penetration properties. BPD-MA is lipophilic, a potent photosensitizer, and appears to be phototoxic to neovascular tissues and tumors.

In a preferred embodiment, the green porphyrin is prepared as a liposomal preparation or is coupled to a ligand that binds to a specific surface component of the neovasculature to improve even further its effectiveness as a photosensitizer. Preferably, the ligand comprises an antibody or an immunologically reactive fragment thereof. The capacity for selective localization of a green porphyrin can also be improved by coupling to a carrier molecule that potentially delivers higher concentrations of the green porphyrin to the target tissue.

A carrier that is appropriate for clinical use is human low-density lipoprotein (LDL). Human LDL is a physiologic serum protein metabolized by cells via uptake by high affinity receptors. LDL exhibits desirable characteristics as a selective carrier because LDL metabolism is increased in tumor cells. Neoplastic tissues and neovascularization have been shown to have increased numbers of LDL receptors. Further, by increasing the partitioning of the green porphyrin into the lipoprotein phase of the blood, it appears to be delivered more efficiently to the target tissue.

Because of its lipophilicity and negative charge, green porphyrins strongly interact with lipoproteins. Most preferably, the green porphyrin is complexed with low density lipoprotein (LDL).

When injected intravenously, BPD-MA is cleared from the bloodstream with a half-life of about 10–30 minutes, with the highest tissue levels being reached in about three hours after administration by injection and declining rapidly in the first 24 hours. BPD-MA is cleared primarily via bile and feces (60%), with only 4% being cleared via the kidneys and urine. Thus, skin photosensitivity occurs with BPD-MA only transiently, with minimal reactivity after 24 hours in in vivo models.

The green porphyrin can be administered in any of a wide variety of ways, for example, orally, parenterally, or rectally. Parenteral administration, such as intravenous, intramuscular, or subcutaneous, is preferred. Intravenous injection is especially preferred.

The dose of green porphyrin can vary widely depending on the tissue to be treated; the physical delivery system in which it is carried, such as in the form of liposomes, or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in photodynamic therapy, and the time interval between administration of the dose and the therapeutic irradiation. All of these parameters should be adjusted to produce significant damage to neovascular or tumor tissue without significant damage to the surrounding tissue or, on the other hand, to enable the observation of blood vessels in the eye without significant damage to the surrounding tissue. Typically, the dose of green porphyrin used is within the range of from about 0.1 to about 20 mg/kg, preferably from about 0.15–2.0 mg/kg, and even more preferably from about 0.25 to about 0.75 mg/kg.

Specifically, as the green porphyrin dose is reduced from about 2 to about 1 mg/kg, the fluence required to close choroidal neovascular tissue tends to increase, for example, from about 50 to about 100 Joules/cm$^2$.

After the photosensitizing green porphyrin has been administered, the choroidal neovascular tissue or tumor being treated or observed in the eye is irradiated at the wavelength of maximum absorbance of the green porphyrin, usually between about 550 and 695 nm. A wavelength in this range is especially preferred for enhanced penetration into bodily tissues.

As a result of being irradiated, the green porphyrin in its triplet state is thought to interact with oxygen and other compounds to form reactive intermediates, such as singlet oxygen, which can cause disruption of cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to endothelial cells, with subsequent platelet adhesion, degranulation, and thrombus formation.

The fluence during the irradiating treatment can vary widely, depending on type of tissue, depth of target tissue, and the amount of overlying fluid or blood, but preferably varies from about 50–200 Joules/cm$^2$.

The irradiance typically varies from about 150–900 mW/cm$^2$, with the range between about 150–600 mW/cm$^2$ being preferred. However, the use of higher irradiances may be selected as effective and having the advantage of shortening treatment times.

The optimum time following green porphyrin administration until light treatment can vary widely depending on the mode of administration; the form of administration, such as in the form of liposomes or as a complex with LDL; and the type of target tissue. As a specific example, a time interval of 1–20 minutes is often appropriate for retinal neovascular tissue, about 120 minutes is allowed for choroidal neovascular tissue, and up to about three hours may be allowed for tumors. Thus, effective vascular closure generally occurs at times in the range of about one minute to about three hours following administration of the green porphyrin.

The time of light irradiation after administration of the green porphyrin may be important as one way of maximizing the selectivity of the treatment, thus minimizing damage to structures other than the target tissues. For a primate, it is believed that the green porphyrin begins to reach the retinal vasculature by about 7–15 seconds following administration. Typically, the green porphyrin persists for a period of about 5–15 minutes, depending on the dose given. Treatment within the first five minutes following administration of the green porphyrin should generally be avoided to prevent undue damage to retinal vessels still containing relatively high concentrations of the green porphyrin.

Clinical examination and fundus photography typically reveal no color change immediately following photodynamic therapy, although a mild retinal whitening occurs in some cases after about 24 hours. Closure of choroidal neovascularization, however, is preferably confirmed histologically by the observation of damage to endothelial cells.

Vacuolated cytoplasm and abnormal nuclei can become apparent as early as 1–2 hours following photodynamic therapy, with disruption of neovascular tissue typically becoming more apparent by about 24 hours after light treatment. Associated damage to the retinal pigment epithelium (RPE), pyknotic nuclei in the outer nuclear layer, and loss of photoreceptors may also be observed. However, the inner retina usually appears relatively undamaged, as shown by control studies using photodynamic therapy with BPD-MA on a normal retina and choroid showing no damage to large choroidal and retinal vessels.

Closure can usually be observed angiographically by about 40 seconds to a minute in the early frames by hypofluorescence in the treated areas. During the later angiographic frames, a corona of hyperfluorescence begins to appear and then fills the treated area, possibly representing leakage from the adjacent choriocapillaris through damaged retinal pigment epithelium in the treated area. Large retinal vessels in the treated area perfuse following photodynamic therapy, but tend to demonstrate late staining.

Minimal retinal damage is generally found on histopathologic correlation and is dependent on the fluence and the time interval after irradiation that the green porphyrin is administered. Histopathologic examination usually reveals vessel remnants in the area of choroidal neovascular tissue, but the retinal vessels typically appear normal. Further, there is no indication of systemic toxicity, and cutaneous photosensitization does not appear to develop.

As a result of the invention, photodynamic therapy can be used more selectively, relying on the low intensity light exposure of green porphyrins that have become localized within vascular tissue. Complications, suck as serous detachment and hemorrhage, are not noted with the invention. Thus, photodynamic therapy with a green porphyrin appears to have broad application to clinical ophthalmology in treating such diseases as age-related macular degeneration, neovascular glaucoma, and persistent disc neovascularization in diabetic retinopathy.

Photodynamic therapy using a green porphyrin can also be used advantageously to treat not only nonpigmented tumors, but also pigmented intraocular tumors such as pigmented choroidal melanomas, and other pigmented tumors of the choroid, retina, iris or cornea. The administered green porphyrin accumulates within the neoplastic lesion and, upon localized light exposure at an appropriate wavelength, the tumor tissue is thought to be irreversibly damaged by the interaction with active molecular species like singlet oxygen and other radicals induced by photoactivated dye molecules. Maximal efficiency in tumor destruction, combined with minimal irritation to adjacent physiological structures is a major benefit in the treatment of intraocular malignancies, in particular, choroidal tumors, which are in close contact with sensitive neuronal and vascular structures.

Light microscopic evaluation of tumors that have not been treated with photodynamic therapy show a mass of polygonal cells. Cell nuclei are typically vesicular with prominent nucleoli, and mitotic figures are scattered throughout the microscopic field. Tumors typically exhibit many thin-walled blood vessels, which are cylindrical in shape, are lined with intact endothelial cells, and contain few erythrocytes.

After photodynamic therapy with a green porphyrin, however, tumor blood vessels become dilated and densely packed with erythrocytes. The tumor demonstrates clotted erythrocytes within the vascular lumina. Several days later, homogeneous necrosis is typically observable throughout the lesion. The tumor cells begin to exhibit hyperchromatic nuclei and loss of cytoplasmic features. Further, vascular structures show disintegration and endothelial cell loss.

In treating tumors, the green porphyrin dosage administered may vary widely depending on other parameters, as described above but, preferably, is within the range of 0.5 to 3 mg/kg. The radiant exposure can also range widely, depending on the pigmentation and size of the tumor, but typically is in the range from about 60 to about 2600 J/cm$^2$. The level of light exposure is of particular interest with respect to the time duration of the treatment.

In addition, green porphyrin can be used to observe the condition of blood vessels in the eye, either alone or used in concert with other dyes such as fluorescein or indocyanine green, as described above to follow the progress of destruction choroidal neovascular or tumor tissue. In such angiographic systems, a sufficient amount of green porphyrin is administered to produce an observable fluorescent emission when excited by light, preferably light having a wavelength in the range of about 550–700 nm. Images are recorded by illuminating the eye with light in the excitation wavelength range and detecting the amount of fluorescent light emitted at the emission wavelength. A preferred camera, which both emits and receives light in the 550–700 nm range, is the TopCon 50VT camera in the Ophthalmic Imaging System (Ophthalmic Imaging System Inc., 221 Lathrop Way, Suite 1, Sacramento Calif.). An alternative camera is the TopCon camera TRC 50IA connected to the TopCon Imagenet System (TopCon America Corporation, 65 West Century Road, Taramus N.J.).

In a preferred observation method of the invention, the green porphyrin is administered, preferably by intravenous injection of a bolus followed by a saline flush. The green porphyrin typically reaches the retinal vasculature in about 7–15 seconds, and the early angiographic frames are recorded after the first 20 seconds, one every 3–5 seconds. Additional frames are taken periodically for about two hours. A typical protocol might call for the image to be recorded at about 40 seconds, then at 50 seconds, 60 seconds, two minutes, 5 minutes, 10 minutes, 20 minutes, 40 minutes, 60 minutes, and two hours.

A camera is usually used to collect the emitted fluorescent light, digitize the data, and store it for later depiction on a video screen, as a hard paper copy, or in connection with some other imaging system. While a film recording device may be used when additional dyes such as fluorescein are being used in combination with the green porphyrin, a CCD camera (video recording device) is preferable as being able to capture emissions at higher wavelengths, thus producing greater tissue penetration. As a result, one can obtain more sophisticated information regarding the pattern and extent of vascular structures in different ocular tissue layers, giving the ability to detect the "leakiness" that is characteristic of new or inflamed blood vessels. Further, it is preferable to use a camera that is capable of providing the excitation light, appropriately filtered to deliver only light of the desired excitation wavelength range, and then to capture the emitted, fluorescent light with a receiving device, appropriately filtered to receive only light in the desired emission wavelength range.

The following examples are to illustrate but not to limit the invention.

EXAMPLE 1

Control of Experimental Choroidal
Neovascularization Using PDT with BPD-MA/LDL
at Low Irradiance Cynomolgus monkeys weighing 3–4 kg were anesthetized with an intramuscular injection of ketamine hydrochloride (20 mg/kg), diazepam (1 mg/kg), and atropine (0.125 mg/kg), with a supplement of 5–6 mg/kg of ketamine hydrochloride as needed. For topical anesthesia, proparacaine (0.5%) was used. The pupils were dilated with 2.5% phenylephrine and 0.8% tropicamide.

Choroidal neovascularization was produced in the eyes of the monkeys using a modification of the Ryan model, in which burns are placed in the macula, causing breaks in Bruch's membrane, with a Coherent Argon Dye Laser #920, Coherent Medical Laser, Palo Alto, Calif. (Ohkuma, H. et al. *Arch. Ophthalmol.* (1983) 101:1102–1110; Ryan, S. J. *Arch Ophthalmol* (1982) 100:1804–1809). Initially, a power of 300–700 mW for 0.1 seconds was used to form spots of about 100 µm, but improved rates of neovascularization were obtained with 50µ spots formed using a power of about 300–450 mW for 0.1 second.

The resulting choroidal neovascularizations were observed by (1) fundus photography (using a Canon Fundus CF-60Z camera, Lake Success, Long Island, N.Y.); (2) by fluorescein angiography (for example, by using about 0.1 ml/kg body weight of 10% sodium fluorescein via saphenous vein injection); and (3) histologic examination by light and electron microscopy.

Immediately before use, BPD-MA was dissolved in dimethyl sulfoxide (Aldrich Chemical Co., Inc., Milwaukee, Wis.) at a concentration of about 4 mg/ml. Dulbeccos phosphate buffered salt solution (Meditech, Washington, D.C.) was then added to the stock to achieve a final BPD concentration of 0.8 mg/ml. Human low-density-lipoprotein (LDL) prepared from fresh frozen plasma was added at a ratio of 1:2.5 mg BPD-MA:LDL. The green porphyrin dye and dye solutions were protected from light at all times. After mixing, the dye preparation was incubated at 37° for 30 minutes prior to intravenous injection. The monkeys were then injected intravenously via a leg vein with 1–2 mg/kg of the BPD-MA complexed with LDL over a five-minute period, followed by a flush of 3–5 cc of normal saline.

Following this intravenous injection, the eyes of the monkeys were irradiated with 692 nm of light from an argon/dye laser (Coherent 920 Coherent Medical Laser, Palo Alto, Calif.), using a Coherent LDS-20 slit lamp. The standard fiber was coupled to larger 400 µm silica optical fiber (Coherent Medical Laser, Pal Alto, Calif.) to allow larger treatment spots as desired. Seventeen (17) areas of choroidal neovascularization were treated using a 1250 µm spot. Treatment spot sizes were confirmed at the treatment plane using a Dial caliper micrometer. Some areas of choroidal neovascularization were treated with several adjacent treatment spots to treat the whole area of choroidal neovascularization. One large choroidal neovascular membrane was treated with photodynamic therapy to the nasal half only.

The photodynamic irradiation treatments were carried out with a plano fundus contact lens (OGFA, Ocular Instruments, Inc., Bellvue, Mass.). Power was verified at the cornea by a power meter (Coherent Fieldmaster, Coherent, Auborn, Calif.). The fluence at each treatment spot was 50, 75, 100 or 150 Joules/cm$^2$. Initially, the irradiance was set at 150 mW/cm$^2$ to avoid any thermal effect but, as the experiment proceeded, the irradiance was increased to 300 mW/cm$^2$ or 600 mW/cm$^2$ to reduce the treatment duration time. The time interval between injection of the green porphyrin dye and the treatment irradiating step ranged from about 1 to about 81 minutes.

A number of different combinations of parameter values were studied and are summarized below in Table 1:

TABLE 1

| IRRADIANCE AT 150 mW/cm$^2$ | | | | | |
|---|---|---|---|---|---|
| Number of CNV Treated | Dye dose (mg/kg) | Fluence (J/cm$^2$) | Duration of Treatment (mins) | Time after Injection (mins) | Closure by Angiography |
| 2 | 2 | 50 | 5.6 | 18, 38 | 2/2 |
| 1 | 2 | 75 | 8.3 | 81 | 1/1 |
| 1 | 2 | 100 | 11.2 | 22 | 1/1 |
| 2 | 1 | 50 | 5.6 | 5, 30 | 0/2 |
| 3 | 1 | 100 | 11.2 | 1, 2 and 5 | 3/3 |
| 4 | 1 | 150 | 16.6 | 14–43 | 3/4 |

"Dye only" controls, which were exposed to dye but not to laser light, were examined in the areas of normal retina/choroid. Areas of choroidal neovascularization were examined angiographically and histologically. "Light only" controls were not performed, since the irradiances used for photodynamic therapy were well below the levels used for clinical laser photocoagulation. (In a related experiment, a minimally detectable lesion using "light-only" required an irradiance of 37 W/cm$^2$, about 100 times the light levels used for photodynamic therapy.)

Following photodynamic therapy, the monkeys were returned to an animal care facility. No attempt was made to occlude the animals' eyes, but the room in which they were housed was darkened overnight.

The condition of the choroidal neovasculature was followed by fundus photography, fluorescein angiography, and histologic examination. In particular, the eyes of the monkeys were examined by fluorescein angiography acutely and at 24 hours after the photodynamic therapy was given. In some cases, follow-up by fluorescein angiography was performed at 48 hours and at one week, until the eyes were harvested and the animals killed at the following time points: acutely, at 24 hours, 48 hours, and 8 days following photodynamic therapy. Animals were sacrificed with an intravenous injection of 25 mg/mg Nembutal.

To perform the histologic examination, all eyes were enucleated under deep anesthesia and fixed overnight in modified Karnovsky's fixative, and then transferred to 0.1M phosphate buffer, pH 7.2 at 4° C. Both light microscopy and electron microscopy were used for these studies. For light microscopy, tissue samples were dehydrated, embedded in epon and serially sectioned at one micron. The sections were stained with tolnizin blue and examined with an Olympus photomicroscope. For electron microscopy, tissue samples were post-fixed in 2% osmium tetroxide and dehydrated in ethanol. Sections were stained with uranyl acetate in methanol, stained with Sato's lead stain, and examined with a Philips #CM 10 transmission electron microscope.

Using the low irradiance level of 150 mW/cm$^2$ to minimize any thermal component of the treatment, green porphyrin doses of 1–2 mg/kg of BPD-MA/LDL, and fluences of 50–150 Joules/cm$^2$, choroidal neovascularization was effectively closed. Using the higher 2 mg/kg dose effectively closed choroidal neovascularizations at even the lowest 50 Joules/cm$^2$ fluence. When the green porphyrin dose was decreased to 1 mg/kg of BPD-MA/LDL to minimize damage to surrounding tissues, the fluence required to effectively close choroidal neovascular tissue increased to 100 Joules/cm$^2$. At 100 and 150 Joules/cm$^2$, the treated choroidal neovascular tissue was angiographically closed, as shown by hypofluorescence in the area of treatment.

Prior to photodynamic therapy, the areas of choroidal neovascularization exhibited a gray sub-retinal elevation that leaked profusely on fluorescein angiography. There was no apparent color change in the treated areas either during or immediately after photodynamic treatment. However, 24 hours after the irradiating step, there was mild retinal whitening in the treated areas.

Further fluorescein angiography showed hypofluorescence in the treated areas, with no apparent filling of the associated neovascular tissues. Retinal vessels within the treated areas were perfused, but stained later. A hyperfluorescent rim at the border of the treated area was apparent in the later frames of the angiograph, and the rim then progressed to fill the treated area. Although mild staining of retinal vessels was noted angiographically, no complications, such as serous retinal detachment or hemorrhage, were noted.

On histopathologic examination of the 2 mg/kg dose samples, there was marked disruption of the treated choroidal neovascular tissue with disrupted endothelial cells. The choriocapillaris was also occluded. Although large choroidal vessels were unaffected, extravasated red blood cells were noted in the choroid. Retinal pigment epithelium (RPE) damage was noted as well with vacuolated cells, with the outer nuclear layer demonstrating pyknotic nuclei and disrupted architecture. No histologic abnormality of the retinal vessels was seen.

Histolopathologic examination of the 1 mg/kg dose samples showed damage to endothelial cells in the choroidal neovascular tissue, with abnormal nuclei and disrupted cytoplasm in the endothelial cells. The lumens of the vessels in the choroidal neovascular tissue were occluded by fibrin acutely and were closed by 24 hours after treatment. Closure of the choroicapillaris was also noted. At 24 hours, the retinal pigment epithelium (RPE) appeared abnormal with vacuolated cytoplasm. Pyknotic nuclei in the inner and outer layer indicated damage secondary to the laser injury used to induce the neovascularization in this model. Retinal vessels appeared to be undamaged.

Choroidal neovascular tissue that was treated and followed for eight days showed persistent closure, as shown by hypofluorescence in the early frames of the angiogram. Histologically, the treated areas demonstrated degraded vessel lumens empty of debris. The choriocapillaris was sparse but patent in the treated area. In contrast, areas of choroidal neovascularization not treated by photodynamic therapy demonstrated branching capillaries between Bruch's membrane and the outer retina.

No adverse effects of photodynamic therapy with the green porphyrin were noted. There was no associated serous retinal detachment, retinal or sub-retinal hemorrhage, or post-treatment inflammation. Further, no adverse systemic effects of the dye administration were noted. However, the low irradiance forced treatment times to be long—about 16.6 minutes to yield 150 Joules/cm$^2$.

EXAMPLE 2

Control of Experimental Choroidal Neovascularization Using PDT with BPD-MA/LDL at Higher Irradiances To make clinical treatments shorter, additional experiments were performed using higher irradiance values. Experience with higher irradiance indicated that no thermal damage would take place with irradiances as high as 1800 mW/cm$^2$. Moulton et al., "Response of Retinal and Choroidal Vessels to Photodynamic Therapy Using Benzoporphyrin Derivative Monoacid", *IOVS* 34, 1169 (1993), Abstract 2294-58. Therefore, irradiances of 300 mW/cm$^2$ and 600 mW/cm$^2$ were also used to treat choroidal neovascular tissue in accordance with the procedures described in Example 1. The results showed that shortened treatment times effectively closed the choroidal neovascular tissue, as indicated below in Table 2.

TABLE 2

| | | | IRRADIANCE OVER 150 mW/cm$^2$ | | | |
|---|---|---|---|---|---|---|
| Number of CNV Treated | Dye dose (mg/kg) | Fluence (J/cm$^2$) | Irradiance (mW/cm$^2$) | Duration of Treatment (mins) | Time after Injection (mins) | Closure by Angiography |
| 2 | 1 | 150 | 300 | 8.3 | 5, 53 | 2/2 |
| 2 | 1 | 150 | 600 | 4.7 | 22, 69 | 2/2 |

Occlusion of the choroidal neovascular tissue and subjacent choriocapillaris was observed, as well as damage to the retinal pigment epithelium and outer retina.

EXAMPLE 3

Control of Experimental Choroidal Neovascularization Using PDT with BPD-MA Liposomes The following experiment of photodynamic therapy using a liposomal preparation of BPD-MA was conducted to determine the optimal time interval after intravenous injection as a bolus of the BPD-MA over about 20 seconds, followed by a 3–5 cc saline flush, to begin the irradiating step. Choroidal neovascularization in cynomolgus monkeys was treated to demonstrate efficacy of the photodynamic therapy. Normal choroid tissue was treated to assess relative damage to adjacent tissues.

The monkeys were initially injected with a green porphyrin dose of 1 mg/kg. At predetermined time intervals following this injection, the eyes of the monkeys were irradiated with an irradiance of 600 mW/cm$^2$, and a fluence of 150 J/cm$^2$. The irradiating light was from an argon/dye laser (Coherent 920 Coherent Medical Laser, Palo Alto, Calif.) equipped with a 200 micron fiber adapted through a Laser-Link (Coherent Medical Laser) and a split lamp delivery system (Coherent). Other than these differences, the eye membranes were treated in the same manner as described in Example 1. All areas of treated choroidal neovasculature for all time points after the liposomal BPD-MA injection showed whitening of the retina and early hypofluorescense on fluorescein angiography when measured one week after treatment. On histology, there was evidence of partial closure of choroidal neovasculature at the early time points, no effect at mid-time points, and more effective closure at late irradiation time points, e.g., at 80 and 100 minutes.

The normal choroid treated with the same parameters showed whitening of the retina, early hypofluorescence at all time points, and histologic evidence of choroicapillaris (c-c) accompanied by damage to the choroid and retina, particularly at early time points.

EXAMPLE 4

Using PDT with BPD-MA Liposomes at Lower Green Porphyrin Doses

Using the general procedure of Example 1, additional experiments were performed using the intravenous injection of liposomal BPD-MA at doses of 0.25, 0.5 and 1 mg/kg. Photodynamic therapy was performed with an irradiance of 600 mW/cm², a fluence of 150 J/cm², and a treatment duration of four minutes, nine seconds.

The effects of treatment were assessed by fundus photography and fluorescein angiography, and then confirmed by light and electron microscopy. Photodynamic therapy of normal choroid tissue demonstrated the effect on adjacent structures, such as the retina, while the treatment of choroid neovascular tissue demonstrated efficacy.

Table 3 below describes the lesions produced on normal choroids by administration of 0.5 mg/kg BPD-MA at time points ranging from 5 to 60 minutes:

TABLE 3

| 0.5 mg/kg, NORMAL CHOROID | | |
| --- | --- | --- |
| Time after injection (min) | Fluorescein Angiography | Histology |
| 5 | Hypofluorescence | c-c and large choroidal vessel closure; outer and inner retina damage. |
| 20 | Hypofluorescence; retinal vessels - normal | cc closure; damage to outer retina |
| 40 | Mild early hypofluorescence | cc open (not center of lesion); outer retina damage |
| 60 | Early hypofluorescence; less than the 20-minute lesion described above | cc closed; outer retina damage; inner retina fairly good. |

When 0.5 mg/kg BPD-MA was also used to treat choroidal neovasculature under the same conditions, marked hypofluorescence corresponding to closure of choroid neovasculature was exhibited in areas irradiated at times of 5, 20 and 40 minutes after injection. When 50 minutes after injection were allowed to elapse before photodynamic irradiation was begun, there was less hypofluorescence and presumably less effective closure.

The study was then repeated with the green porphyrin dose decreased to 0.25 mg/kg. Table 4 below describes the lesions produced on normal choroids by treatments with 0.25 mg/kg, 600 mW/cm², and 150 J/cm² at time points ranging from 5 to 60 minutes:

TABLE 4

| 0.25 mg/kg, NORMAL CHOROID | | |
| --- | --- | --- |
| Time after injection (min) | Fluorescein Angiography | Histology |
| 10 | Early hypofluorescence | c-c closure; choroidal vessel - normal; RPE damaged; retinal vessels - normal; mild damage to outer retina |
| 20 | Early hypofluorescence | Same as 10-minute lesion above |
| 40 | Faint early hypofluorescence; late staining | Patchy cc closure; less damage to RPE and outer retina |

TABLE 4-continued

| 0.25 mg/kg, NORMAL CHOROID | | |
| --- | --- | --- |
| Time after injection (min) | Fluorescein Angiography | Histology |
| 60 | Not demonstrated | No effect on cc; mild vacuolization of RPE |

When the above study was repeated using the same green porphyrin dose of 0.25 mg/kg and irradiance of 600 mW/cm², but with a reduced fluence of 100 J/cm², the same angiographic and histologic pattern was exhibited as described above. However, cc was open in the 40-minute lesion.

In the last portion of these experiments, a green porphyrin dose of 0.25 mg/kg was used to treat experimental choroidal neovascularization with an irradiance of 600 mW/cm² and a fluence of 150 J/cm² at elapsed time points ranging from 5 to 100 minutes. This combination of conditions caused effective cc closure with only minimal damage to the outer retina. The results are shown in Table 5 below:

TABLE 5

| 0.25 mg/kg, PDT over CNV | | |
| --- | --- | --- |
| Time after injection (min) | Fluorescein Angiography | Histology |
| 5 | Early hypofluorescence | Partially closed CNV; c-c closed; damage to inner retina |
| 20 | Early hypofluorescence; less than the 5-minute lesion | CNV - open vessel, fibrin and clots; inner retina looks fine |
| 30 | Some hypofluorescense next to CNV | Minimal effect on CNV |
| 40 | Hypofluorescence; questionable change compared to previous reaction | Minimal effect on CNV |
| 60 | Hypofluorescence | Minimal effect on CNV |
| 80 | Hypofluorescence | Partial closure of CNV; retina over CNV looks intact |
| 100 | Hypofluorescence | CNV partially closed |

Thus, fluorescein angiography and histopathology in the above series of experiments demonstrated early hypofluorescence at early time points. Further, the histopathology study showed partial CNV closure at all time points after injection using 80 and 100 minutes as the post-injection interval before the irradiating treatment.

In summary, acceptable destruction of choroidal neovascular tissue at all tested doses of BPD-MA was shown by fluorescein angiography and histology. However, the lower doses appeared to increase selectivity, as assessed by treatment of a normal choroid. Effective choriocapillaris closure in normal choroids with minimal retinal damage was produced by irradiating at a time about 10 minutes, 20 seconds after injection of the green porphyrin at a dose of 0.25 mg/kg. By adjusting the dose, the time of irradiation after green porphyrin injection, and fluence, one can improve even further the selectivity of the green porphyrin. However, the liposomal preparation of BPD-MA was clearly demonstrated to be a potent photosensitizer.

We claim:

1. An angiographic method to observe the condition of blood vessels, including neovasculature in the eye of an intact living primate, which method comprises:
   a. administering to said primate comprising at least one eye for which said observation is desired and containing said neovasculature an amount of green porphyrin which will provide an observable amount of green porphyrin in the blood vessels and neovasculature of said eye;
   b. permitting sufficient time to elapse so that an observable amount of said green porphyrin resides in the blood vessels and neovasculature of the eye; and
   c. applying light of a wavelength in the range of about 550–700 nm to the eye so as to effect fluorescence of the green porphyrin; and
   d. detecting said fluorescence with a suitable camera.

2. The method of claim 1 wherein said green porphyrin is a BPD.

3. The method of claim 2 wherein said BPD is BPD-MA.

4. The method of claim 1 wherein said green porphyrin is complexed with low-density lipoprotein.

5. The method of claim 1 wherein said green porphyrin is contained in a liposomal preparation.

6. The method of claim 3 wherein said BPD-MA is contained in a liposomal preparation.

* * * * *